United States Patent [19]

Papantoniou et al.

[11] Patent Number: 4,844,889

[45] Date of Patent: Jul. 4, 1989

[54] COSMETIC COMPOSITION CONTAINING AN AMIDE-AMINE TYPE CONDENSATE, AND A COSMETIC TREATING PROCESS USING SAID CONDENSATE

[75] Inventors: Christos Papantoniou, Montmorency; Claude Mahieu, Paris, both of France

[73] Assignee: L'Oreal, Paris, France

[21] Appl. No.: 881,279

[22] Filed: Jul. 2, 1986

[30] Foreign Application Priority Data

Jul. 3, 1985 [FR] France ............................... 85 10158
Jun. 19, 1986 [FR] France ............................... 86 08858

[51] Int. Cl.$^4$ ..................... A61K 7/00; A61K 7/06; A61K 7/48
[52] U.S. Cl. ........................................ 424/70; 424/71; 424/78; 424/81; 424/DIG. 2; 252/DIG. 13
[58] Field of Search ..................... 523/105; 424/81, 70, 424/71, 59, 78, DIG. 2

[56] References Cited

U.S. PATENT DOCUMENTS 3,351,622 11/1967 Tesoro .
3,865,723 2/1975 Marchisio et al. .............. 525/54.1 X
4,013,787 3/1977 Vanlerberghe et al. .
4,172,887 10/1979 Vanlerberghe et al. .............. 424/81
4,668,273 5/1987 Haase ................................ 424/78 X

FOREIGN PATENT DOCUMENTS 2186253 1/1974 France .
2098226 11/1982 United Kingdom .
2177916 2/1987 United Kingdom .

OTHER PUBLICATIONS

Yoshio Imai et al., "Synthesis of Polyamide-Amines by Polyaddition of Aromatic Diamines in N,N'-Methylenediacrylamide" Makromol. Chem., Rapid Commun. 2, 173-175 (1981).
"Synthesis and Characterization of Poly (Amide-Amine) Polymers", J. Polym. Sci. Polym. Chem. Ed., vol. 22, 985-994 (1984).
Journal of Polymer Science: Polymer Letters Edition, vol. 21, 1983, pp. 413-415, John Wiley & Sons, Inc.; E. Shchori: "Poly (Secondary Amine)s from Diacrylates and Diamines."

Primary Examiner—Ellis P. Robinson
Assistant Examiner—Susan S. Rucker
Attorney, Agent, or Firm—Cushman, Darby & Cushman

[57] ABSTRACT

A cosmetic composition for improving the suppleness of the skin or hair and for protecting the keratin of the skin or hair from degradation by atmospheric agents or light comprises in a cosmetic or dermatologic acceptable vehicle a saturated condensate resulting from the polyaddition of a bis-acrylamide and a sterically hindered primary diamine, the condensate being saturated by hydrogenation or by addition of a thiol or an amine on the double bonds of the acrylamide residue.

6 Claims, No Drawings

COSMETIC COMPOSITION CONTAINING AN AMIDE-AMINE TYPE CONDENSATE, AND A COSMETIC TREATING PROCESS USING SAID CONDENSATE

The present invention relates to dermatologic and cosmetic compositions containing an amide-amine type condensate, these compositions being quite particularly intended for application to the skin or hair.

The condensates, which can be mono or polycondensates, find numerous uses in the field of cosmetics either as a principal component or as a secondary component.

These condensates, when they are employed in compositions for the skin, such as emulsions, improve principally the consistency and texture of the composition and impart more suppleness to the skin.

The polycondensates, or polymers, constitute the components of choice for compositions for the hair, such as hair setting lacquers or lotions, in the measure where they have excellent lacquering power and impart to the hair suppleness without observing the formulation pellicules or a sticky effect which can be due to a strong uptake of moisture by the polymer.

As a function of their degree of condensation, the condensates can provide a particularly wide range of compounds which are capable of being suitably employed in a large number of cosmetic formulations.

Moreover, the amide-amine type polycondensates (or polyamino-amides) of the present invention can be employed as protective agents for the keratin of the hair and skin against atmospheric aggressions and in particular against light.

It has been known for a long time that light is an aggressive agent vis-a-vis the keratin of the hair and skin. For example, numerous publications report that natural light destroys certain amino acids of the hair and that by altering the capillary fiber, it reduces mechanical properties of the hair. By reducing the mechanical properties of hair is meant, principally, a reduction of 15% extension degree and of the load at rupture when the hair is wet.

The 15% of extension degree is the weight that is necessary to apply to moistened hair of a given length to elongate it 15%. The more the weight is increased, the more the hair is elastic and resistant.

The load at rupture when the hair is wet is the weight that is necessary to apply to moistened hair, of a given length, so that it breaks.

To combat against the agression of the keratin of the hair by light, there has already been proposed the use of substances capable of filtering light rays. In particular, there have been employed well known filtering agents, such as benzophenone derivatives, for example, 2-hydroxy-4-methoxy benzophenone or even dibenzoylmethane derivatives, for example 4-tert-butyl-4'-methoxy dibenzoyl methane.

However, these filtering materials have not proven effective in the preservation of the mechanical properties of hair, i.e. its elasticity and its resistance when moistened, vis-a-vis light.

It is apparent, on the other hand, that their presence in certain cosmetic compositions can even accentuate the degradation of the mechanical properties of hair, principally, a reduction of the 15% of extension degree and the load at rupture properties.

The applicants have now discovered that, in a surprising fashion, certain polyaminoamides can preserve the mechanical properties of hair against degradation by light. This property has been evidenced by exposure to natural light (sunlit medium) and to artificial light (xenon transmission by an accelerated aging apparatus of the SUNTEST HANAU type).

The present invention thus relates to, as a new industrial product, a cosmetic composition, aqueous or anhydrous, containing as a principal or secondary component, at least one saturated condensate resulting from the addition reaction between (1) a bis-acrylamide of the formula:

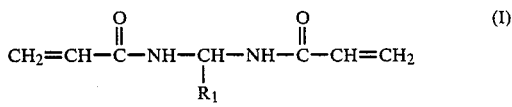

wherein
$R_1$ represents hydrogen or lower alkyl having 1-4 carbon atoms, and (2) at least one sterically hindered primary diamine, of the formula $$NH_2\text{-}R\text{-}NH_2 \qquad (II)$$

wherein
R represents a radical selected from the group consisting of

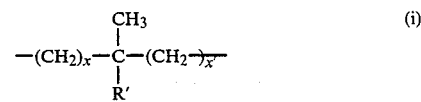

wherein x and x' are 0 or 1 and R' is hydrogen or methyl,

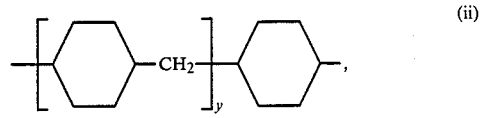

wherein y is 0 or 1,

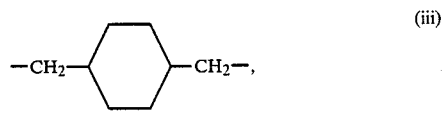

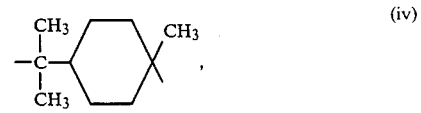

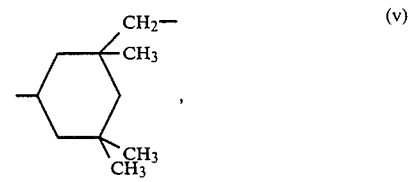

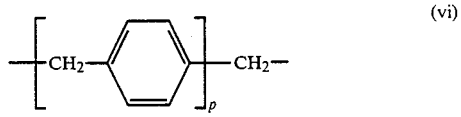

wherein p is 1 or 2, and

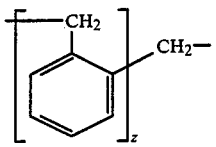

(vii)

wherein z is 1 or 2, the said condensate being saturated by hydrogenation or by addition of a thiol or an amine on the double bonds of the acrylamide residues.

The condensates and, more particularly, the polycondensates, to be advantageously employed as cosmetic agents in accordance with the present invention, must be free from terminal double bonds, which can result from an incomplete reaction of the bisacrylamide (I) initial reaction, so as to avoid their addition to the amine functions of neighboring chains.

In effect, when the condensates are in aqueous solution, without having been previously saturated, they are poorly stable and they rapidly lead to gelification as a result of a reaction between unsaturated terminal functions and terminal amine functions.

Studies undertaken have shown that the saturation of the double bonds with, principally, cysteine avoids this gelification phenomenon and provides, moreover, polymers possessing good cosmetic properties.

The condensates, such as defined above, have preferably a molecular mass between 335 and 200,000, measured by the tonometry method or by the light diffusion method.

Representative sterically hindered diamines of Formula II, capable of leading to a selective addition reaction, include the following:

2,2-dimethyl-1,3-diamino propane,
1,1-diamino ethane,
1,4-diamino cyclohexane,
2,2-diamino propane,
1,2-diamino-2-methyl propane,
(3-amino methyl-3,5,5-trimethyl)cyclohexylamine,
2-amino-2-(4-amino-4-methyl) cyclohexyl propane,
bis-(4-amino cyclohexyl) methane,
1,4-dimethylamino cyclohexane,
1,2-dimethylamino cyclohexane,
$\alpha,\alpha'$-diamino o-xylene,
$\alpha,\alpha'$-diamino p-xylene,
4-bis-benzylamino methane and
2-bis-benzylamino methane.

According to a preferred embodiment of the present invention there is employed in the condensation reaction a mixture of primary diamines, preferably, in a ratio between 40:60 and 60:40.

Representative bis-acrylamides of Formula I which are particularly appropriate include methylene bis-acrylamide, ethylidene bis-acrylamide and propylidene bis-acrylamide.

The condensates, such as defined above, can be employed in the form of salts, for example hydrochlorides, sulfates or lactates or in the form of quaternary derivatives obtained by a quaternization reaction using methyl iodide, methyl chloride, ethyl bromide, dimethyl sulfate or chloroacetic acid.

If the monocondensates are new, the unsaturated polycondensates have been described in the following publications:

Makromol. Chem., Rapid Commun. 2, 173–175 (1981),

Journal of Polymer Science, Vol. 21, 413–415 (1983) and

Journal of Polymer Science, Vol. 22, 985–994 (1984).

The synthesis of the condensates, useful in the present invention, involves essentially two steps, the first step consisting of a nucleophilic addition reaction of at least one sterically hindered primary amine on a bis-acrylamide and the second step consisting of a hydrogenation reaction or an addition reaction of a thiol or amine on the unsaturated terminal functions.

The first step is carried out in the presence of a solvent and, optionally, an acid catalyst such as acetic acid.

Convenient solvents include, in particular, water, methanol or ethanol. The reaction is preferably carried out with stirring at a temperature between 50° and 100° C and preferably at reflux of the solvent for a time between 2 and 10 hours.

The hydrogenation of the condensate is generally carried out in an aliphatic alcohol such as methanol, in the presence of a hydrogenation catalyst such as Adams platinum.

The addition reaction of a thiol such as cysteine on the unsaturated terminal functions can be carried out after having isolated the unsaturated condensate or, in accordance with a preferred embodiment, in the solvent medium immediately after the addition reaction.

The thiol, added in an aqueous solution, is used in excess relative to the double bonds to be saturated and the reaction is carried out at a temperature between 20° and 50° C for a time between 1 and 24 hours.

After the end of the reaction, the resulting saturated condensate is isolated by precipitation in a non-solvent, filtered and dried.

A preferred embodiment of the present invention comprises the use in cosmetic compositions of a condensate having the following formula:

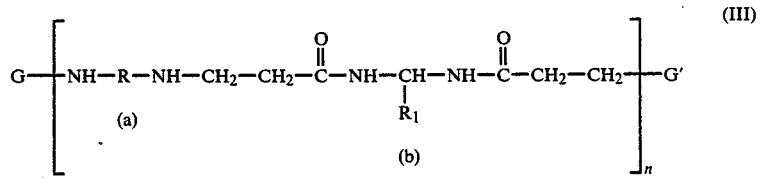

(III)

wherein
R and $R_1$ have the same meanings given above,
G represents hydrogen or

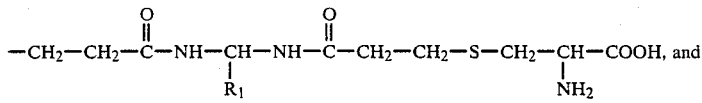

G' represents $-NH-R-NH_2$ or 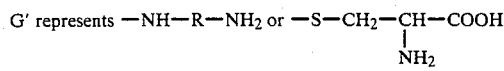

where R has the meaning given above.

The units (a) and (b) represent 50% in moles, the weight percent of the functions derived from cysteine of the formula

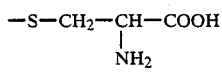

in G and/or G' being between about 0.15 and 30%, and n has an average value between 1 and 200.

Analytical studies, which have been carried out on the condensates of Formula III above, have shown that there is indeed a fixation of the cysteine on the double bonds and that the resulting condensates were stable in solution, principally in an aqueous solution.

In effect, on hydrolysis, using 6N HCl and on analyzing the amino acids using an auto-analyzer (Biotronik LC 500) it has been able to evidence and dose S-carboxyethylcysteine (1) resulting from the hydrolysis according to the following reaction scheme:

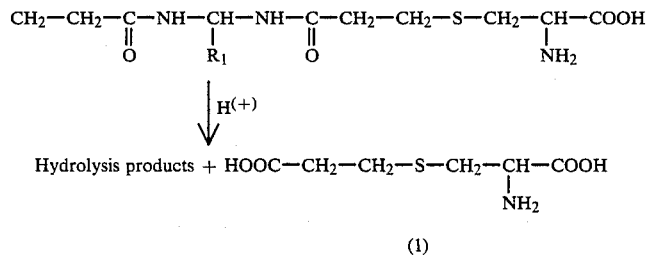

which shows that there is indeed a fixation of cysteine on the double bonds.

In the cosmetic composition according to the present invention, be they aqueous or anhydrous, the concentration of the condensate is generally between 0.1 and 25 weight percent and preferably between 0.5 and 10 weight percent, relative to the total weight of the composition.

These compositions can be aqueous or hydroalcoholic solutions or dispersions (the alcohol being principally a lower alcohol such as ethanol or isopropanol), emulsions, creams, milks, gels or they can be packaged in aerosols (foams or sprays) containing a propellant such as for example nitrogen, nitrogen oxide, or fluorchlorinated hydrocarbons.

In the cosmetic compositions for the hair, the condensates, principally polycondensates, facilitate the production of bouffant coiffures and impart to dry hair qualities of liveliness, a shiny appearance and easy comability. In addition, they protect the hair against atmospheric aggressions and in particular against degradation by light.

The condensates can be present in cosmetic compositions for the hair as an additive or as a principal active component, in hair setting lotions, hair treating compositions, styling lotions, styling creams or gels, or even as an additive in shampoo compositions, rinsing products for application to the hair before or after shampooing, before or after a permanent wave, before or after a hair dyeing operation, hair setting compositions, hair brushing compositions, compositions for permanent waves, hair dyeing, hair bleaching, hair restructuring lotions, antiseborrhea treating lotions and hair lacquer compositions.

The adjuvants or cosmetic agents generally present in the cosmetic compositions used in accordance with the present invention are for example cationic, anionic, amphoteric and non-ionic surface active agents or mixtures thereof, thickening agents, polymers other than the above poly amino-amides, softening agents, preservatives, foam stabilizers, electrolytes, oils, pH regulating agents, waxes, anti-oily agents, sequesterants, perfumes, dyes and synergists.

The cationic, anionic, non-ionic and amphoteric surface active agents and mixtures thereof are generally employed in an amount ranging from 0.1 to 70 weight percent and preferably from 0.5 to 50 weight percent, based on the total weight of the composition.

The cosmetic compositions of the present invention generally have a pH ranging from 2 to 11, and preferably from 3 to 9.

In a general fashion, the thickening agents optionally present in the compositions of the present invention can be sodium alginate, gum arabic or xanthanate gum, cellulosic derivatives such as methyl cellulose, hydroxymethyl cellulose, hydroxyethyl cellulose, hydroxypropyl cellulose, carboxymethyl cellulose or carboxylic polymers such as those known under the trade designation "Carbopol". A thickening of the lotions can also be obtained using a mixture of polyethylene glycol and the stearate or distearate of polyethylene glycol, or by a mixture of phosphoric esters and amides. The concentration of the thickening agent can range from 0.1 to 30 weight percent, preferably from 0.2 to 15 weight percent, based on the total weight of the composition.

The lotions are aqueous or hydroalcoholic solutions having a pH close to neutral and ranging from about 5 to 8.

The treating creams are produced using a support or vehicle based on a soap or fatty alcohol in the presence of an emulsifier. The soaps can be prepared from natural or synthetic fatty acids having 12 to 20 carbon atoms (such as lauric acid, myristic acid, palmitic acid, oleic acid, ricinoleic acid, stearic acid, isostearic acid and mixtures thereof) at concentrations ranging from 10 to 30 percent and alkalizing agents (such as soda, potash, ammonia, monoethanolamine, triethanolamine and mixtures thereof).

The treating gels contain thickening agents such as sodium alginate or gum arabic or cellulosic derivatives in the presence or not of a solvent. The concentration of the thickening agent can range from 0.5 to 30 weight percent and preferably from 0.5 to 15 weight percent.

The solvents employed can be lower aliphatic alcohols, glycols and their ethers, the concentration of these solvents ranging from 2 to 20 weight percent.

The compositions of the present inventions are, in particular, shampoos principally for oily hair, characterized by the fact that they contain at least one condensate such as defined above and at least one cationic, non-ionic, anionic, or amphoteric detergent, or a mixture thereof.

These shampoo compositions can also contain various adjuvants such as for example perfumes, dyes, preservatives, thickening agents, foam stabilizers and softening agents. In these shampoo compositions the concentration of the detergent ranges generally between 2 and 50 percent, in particular from 3 to 50 percent by weight and the concentration of the condensate is preferably between 0.1 and 4 weight percent.

The compositions of the present invention can also include hair setting lotions or hair brushing lotions containing at least one condensate as defined above in an aqueous or hydroalcoholic solution.

Further, the compositions can be applied before or after a shampoo or even between two shampoos thus acting as formulations for the treatment of the hair.

They can, moreover, contain at least one cosmetic resin having anionic or cationic properties. The cosmetic resins useful in such lotions are known and described in cosmetology books.

The compositions of the present invention can also be hair dye compositions containing at least one condensate, such as defined above, and at least one hair coloring agent and a vehicle or support.

The hair dye compositions are preferably gellable liquids; they contain in addition to the condensate, such as defined above, a dye or dye precursor, either polyoxyethylenated or poly glycerolated non-ionic derivatives and solvents, or soaps of liquid fatty acids, such as those of oleic or isostearic acid and solvents. The soaps are soaps of soda, potash, ammonia or mono-, di-, or triethanolamine.

The cosmetic compositions of the present invention which are useful in protecting the hair against degradation by atmospheric agents and light, and containing as active components the polyaminoamides defined above, can be provided in the form of aqueous or hydroalcoholic solutions or dispersions (the alcohol being most often a lower alkanol such as ethanol or isopropanol) thickened or not, creams, gels, aerosol foams or sprays and they can contain adjuvants customarily employed in capillary compositions suitable for the use envisaged.

These compositions, whose use can be, or not, followed by rinsing, can constitute shampoos, after shampoo formulations, rinse products to be applied before or after shampooing, before or after hair dyeing or hair bleaching, before or after a permanent wave or hair straightening operation; non-rinse compositions such as lotions, gels, creams, sprays or foams for setting the hair, for brushing the hair and hair restructuring compositions.

The compositions which are intended to protect the hair against degradation by atmospheric agents and light can contain, for example, from 0.1 to 8 weight percent, and in particular from 0.2 to 3.5 weight percent, of the polyaminoamide such as defined above.

When these cosmetic compositions which are intended to protect the hair constitute compositions not followed by rinsing, the polyaminoamide considered as the active agent protecting the mechanical properties of the hair against light, is present for example in an amount ranging from 0.1 to 5 weight percent relative to the total weight of the composition, and preferably from 0.2 to 2 weight percent.

When the cosmetic compositions which are intended to protect the hair constitute compositions followed by rinsing, the polyaminoamide is present for example in an amount ranging from 0.1 to 8 weight percent and preferably from 0.5 to 3.5 weight percent relative to the total weight of the composition.

These cosmetic compositions which are intended to protect the hair can also include well known cosmetic agents with the proviso that they themselves do not alter the mechanical properties of the keratin of the hair.

When the compositions for the hair in accordance with the present invention constitute non-rinse compositions, i.e. a lotion, cream, gel, foam or spray, for brushing the hair, for setting the hair, for styling the hair or for treating the hair, they include generally, in an aqueous or hydroalcoholic medium, other than the polyaminoamide defined above, at least one cationic, anionic, non-ionic or amphoteric polymer, or a mixture of such polymers, in an amount ranging generally from 0.1 to 10 weight percent, and preferably from 0.1 to 3 weight percent, and optionally anti-foam agents.

When the capillary compositions according to the present invention constitute rinse lotions, also called "rinses" they are applied before or after hair bleaching, before or after a permanent wave, before or after a shampoo or between two shampoos. They are then rinsed after a suitable contact time with the hair.

These compositions can be aqueous or hydroalcoholic solutions containing, optionally, surface active agents; they can also be emulsions or gels. These compositions can also be pressurized in aerosol containers.

In these rinse compositions, the concentration of the surface active agents can range from 0.1 to 10 weight percent and preferably from 0.5 to 7 weight percent. They can also contain non-ionic, cationic, anionic or amphoteric polymers.

When the capillary compositions are provided in the form of gels, to be rinsed or not, they contain thickening agents, in the presence or not of solvents.

The pH of the rinse lotions can vary between 2 and 10 and preferably between 3 and 8.

The cosmetic compositions for the hair according to the present invention before being applied to sensitized hair include advantageously an electrolyte.

The presence of the electrolyte in the composition reduces or suppresses the tendency that sensitized hair has to fix the polymers durably. Useful electrolytes include alkali or alkaline earth salts, soluble in water, of mineral or organic acids, and preferably the chlorides and acetates of sodium, potassium, ammonium and calcium. The amount of electrolyte is preferably between 0.01 and 5 weight percent, advantageously between 0.4 and 3 weight percent, relative to the total weight of the composition.

The compositions according to the present invention which are intended for the treatment of the skin are provided preferably in the form of creams, milks, emulsions, gels or aqueous or hydroalcoholic solutions.

The concentration of the condensate in these compositions can range from 0.1 to 10 weight percent and preferably from 0.25 to 5 weight percent. Adjuvants generally present in these compositions are for example perfumes, dyes, preservatives, thickening agents, sequesterants, emulsifiers, sun screen agents and the like.

These compositions impart to the skin an agreeable soft-to-the-touch property and render the skin supple.

These compositions constitute, principally, treating creams or lotions for the hands and face, sun screen creams, dye creams, make-up remover milks, bath foam liquids, after-shave lotions, toilet water, shaving foams, make-up sticks, colored or non-colored sticks, principally for the lips, for make-up or body hygiene or even deodorant compositions.

The condensates such as defined above can be provided in compositions for the treatment of the skin either as an additive or as a principal active component.

These compositions for the skin can also contain various active substances such as sun screen agents, cicatrizing agents and the like, and are provided in the form of aqueous or hydroalcoholic solutions, creams, milks and the like.

The present invention also relates to a cosmetic treatment process comprising applying to the skin or hair at least one condensate such as defined above in a cosmetically acceptable vehicle.

The present invention also relates to the use as a cosmetic agent, which improves principally the suppleness of the skin and hair, and to protect the keratin of the skin and hair against degradations by atmospheric agents and light, of at least one condensate such as defined above.

In order to better understand the invention, there are given hereafter, as a non-limiting illustration, several examples of the preparation of the condensates, as well as several examples of cosmetic compositions containing them.

EXAMPLE

Polycondensate obtained by polyaddition of bis-(4-amino cyclohexyl) methane and methylene bis-acrylamide and saturation using cysteine.

(a) In a 2 liter round bottom flask, fitted with a stirrer and condenser, there are introduced 600 g methanol and 154 g of methylene bis-acrylamide. The mixture is brought to the reflux of the solvent at which point there are introduced over a 10 minute period, 210 g of bis-(4-amino cyclohexyl) methane. The reaction mixture is heated for 2 hours at reflux. The viscosity of the reaction mixture is 20.4 centipoises (measured at 34.6° C.). The solution is then concentrated until the total weight is 530 g. The compound is precipitated by slowly pouring the reaction mixture into 10 liters of acetone. After filtering and drying the precipitate, the expected amide-amine polycondensate is isolated, providing a yield of 80%.

$\overline{M}_n = 1900$ (measured by tonometry in an ethanol solution).

(b) Treatment with cysteine

In a solution containing 112.5 g of the polycondensate prepared above in part (a) and 187 g of methanol, there is introduced a solution of 5 g of cysteine in 40 g of water. The reaction mixture is heated at 50° C for one hour at which point it is poured into 8 liters of acetone. After filtering and drying the resulting precipitate the expected saturated condensate is obtained.

(c) Determination of the structure of the condensate.

2 g of the condensate obtained in part 1(b) are hydrolyzed with 6N HCl in a sealed ampoule for 4 hours. The resulting solution is then analyzed with an amino acid autoanalyzer sold under the trade designation Biotronik LC 5000.

The absence of cysteine shows that the excess not having reacted with the condensate has been eliminated during purification.

The presence of S-carboxyethylcysteine shows that there has indeed been a fixation of the cysteine. The amount of S-carboxyethylcysteine has been determined as being 0.034 mole per 100 g of condensate or 4.12 g of cysteine fixed per 100 g of condensate.

EXAMPLE 2

Polycondensate obtained by polyaddition of 2,2-dimethyl-1,3-propane and methylene bis-acrylamide, and saturation with cysteine.

In accordance with the same procedures as those described in Example 1, 154 g of methylene bis-acrylamide are reacted with 102 g of 2,2-dimethyl-1,3-propane in 320 g of methanol.

The expected polycondensate is isolated with a 70% yield. As in Example 1(b) the residual double bonds are saturated using cysteine. The viscosity of the resulting polycondensate is 21.9 centipoises (in a 25% solution in water at 34.6° C).

EXAMPLE 3

Polycondensate obtained by polyaddition of 2-amino(4-amino-4-methyl) 2-cyclohexyl propane and methylene bis-acrylamide, and saturation with cysteine.

In accordance with the same procedures as those described in Example 1, 170 g of 2-amino-(4-amino-4-methyl) 2-cyclohexyl propane are reacted with 154 g of methylene bis-acrylamide.

The expected polycondensate is isolated with a 75% yield.

$\overline{M}_n = 840$

As in Example 1(b) the residual double bonds are saturated using cysteine.

EXAMPLE 4

Polycondensate obtained by the polyaddition of (3-aminoethyl-3,5,5-trimethyl) cyclohexylamine and methylene bis-acrylamide, and saturation with cysteine.

In accordance with the same procedures as those described in Example 1, 170 g of (3-aminomethyl-3,5,5-trimethyl) cyclohexylamine are reacted with 154 g of methylene bis-acrylamide.

The expected polycondensate is isolated with a yield of 60%.

$\overline{M}_n = 1300$.

As in Example 1(b) the residual double bonds are saturated using cysteine.

EXAMPLE 5

Polycondensate obtained by the polyaddition of a mixture of 2,2-dimethyl-1,3-diamino propane and bis-(4- amino cyclohexyl) methane with methylene bis-acrylamide, and saturation with cysteine.

In accordance with the same procedures as those described in Example 1, 71.4 g of 2,2-dimethyl-1,3 propane, 63 g of bis-(4amino cyclohexyl) methane and 154 g of methylene bis-acrylamide are reacted together.

The expected polycondensate is isolated with a yield of 70%.

$\overline{M}_n = 1300$.

As in Example 1(b) the residual double bonds are saturated with cysteine.

EXAMPLE 6

Polycondensate obtained by the polyaddition of a mixture of 2,2-dimethyl-1,3-diamino propane (70%) and bis-(4-amino cyclohexyl) methane (30%) with methylene bis-acrylamide and saturation with cysteine.

In a 1 liter reactor, fitted with a stirrer and a condenser, there are introduced 176 g of methanol and 53.40 g of methylene bis-acrylamide. After heating at the reflux of the solvent there is added over a ten minute period a mixture of 24.78 g of 2,2-dimethyl-1,3-diamino propane and 21.82 g of bis-(4-amino cyclohexyl) methane. The reaction is continued for 7 hours. After the end of the polymerization a solution of 8 g of cysteine in 80 g of water is added, and the reaction is continued for 1 hour.

After cooling, the reaction mixture is concentrated to a weight of 320 g and then diluted with 100 g of acetone. This mixture is then slowly poured into 8 liters of acetone.

After filtering and drying 84 g of the expected polycondensate (yield - 84%) having a viscosity of 26.5 centipoises (25% solution in methanol at 4.6° C) are obtained.

EXAMPLE 7

Polycondensate obtained by the polyaddition of a mixture of 2,2-dimethyl-1,3-diamino propane (30%) and bis-(4-amino cyclohexyl) methane (70%) with methylene bis-acrylamide, and saturation with cysteine.

In accordance with the same procedures as those described in Example 6, 9.24 g of 2,2-dimethyl-1,3-diamino propane and 44.3 g of bis-(4-amino cyclohexyl) methane are reacted with 46.47 g of methylene bis-acrylamide in 176 g of methanol.

After the end of the polyaddition, a solution of 8 g of cysteine in 80 g of water is added and the expected polymer is isolated in accordance with the same method.

There are thus obtained, after filtering and drying, 95.5 g of the expected polycondensate (yield - 95.5%) having a viscosity of 45.7 centipoises (25% solution in methanol at 34.6° C).

EXAMPLE 8

Polycondensate obtained by the polyaddition of bis-(4-amino cyclohexyl) methane and methylene bis-acrylamide, acrylamide, and saturation with cysteine.

In accordance with the same procedures as those described in Example 1(a), but extending the time of the polyaddition from 2 hours to 7 hours, and after saturation using cysteine in accordance with the same method as in Example 1(b), there is obtained the polycondensate of Example 1 having a viscosity of 227 centipoises (measured in a 25% solution in water at 34.6° C).

EXAMPLE 9

Polycondensate obtained by the polyaddition of 2,2-dimethyl-1,3-diamino propane and methylene bis-acrylamide, and saturation using cysteine.

In accordance with the same procedures as those described in Example 1(a), but by extending the time of the polyadditon from 2 hours to 7 hours and after saturation using cysteine in accordance with the same method as in Example 1(b), there is obtained the polycondensate of Example 2 having a viscosity of 72.1 centipoises (measured in a 25% solution in water at 34.6° C).

EXAMPLE 10

Polycondensate of Example 2 quaternized with dimethyl sulfate.

In a solution composed of 6.4 g of the polycondensate obtained in accordance with Example 2 and 20 g of methanol, there are introduced 14.6 g of dimethyl sulfate. The reaction mixture is left with stirring for 3 hours at ambient temperature. The reaction mixture is then heated for 3 hours at reflux. The solution is then poured into ethanol and the precipitate is filtered and dried. Analyzing the resulting product shows that 53% of the amine functions of the polycondensate have been quaternized.

EXAMPLE 11

Polycondensate obtained by the polyaddition of 2,2-dimethyl-1,3-diamino propane and methylene bisacrylamide, and saturation with cysteine.

In accordance with the same procedures as those described in Example 6, 38.75 g of 2,2-dimethyl-1,3-diamino propane are reacted with 60 g of methylene bis-acrylamide in 150 g of methanol.

The reaction is maintained at reflux for 7 hours at which point 2.5 g of cysteine in 50 g of water are added. The reaction mixture is then left at reflux of the solvent for 1 hour.

On precipitation using acetone the expected polycondensate having a viscosity of 87 centipoises (in a 25% solution in water at 34.6° C) is obtained.

EXAMPLES OF COMPOSITIONS

EXAMPLE A

A hair setting lotion having the following composition is prepared:

| Polycondensate of Example 2 | 2 g |
|---|---|
| Water, sufficient amount for | 100 g |

The polycondensate, prepared in accordance with Example 2, can be replaced by the same amount of any one of the polycondensates prepared according to Examples 3, 5, 6, 7, 8 and 9.

EXAMPLE B

A hair setting lotion having the following composition is prepared:

| Polycondensate of Example 1(b) | 2 g |
|---|---|
| HCl, 0.1 N, sufficient for pH = 7 | |
| Water, sufficient amount for | 100 g |

The polycondensate, prepared in accordance with Example 1 (b), can be replaced by the same amount of any one of the polycondensates prepared according to Examples 3, 4, 5, 9, 10 and 11.

EXAMPLE C

A hair treating lotion having the following composition is prepared:

| | |
|---|---|
| Polycondensate of Example 1(b) | 1.9 g |
| Ethanol | 50 g |
| Water, sufficient amount for | 100 g |

The polycondensate prepared according to Example 1(b) can be replaced by the same amount of any one of the polycondensates prepared according to Examples 2, 3, 4, 5, 6, 7 and 11.

EXAMPLE D

A body lotion having the following composition is prepared:

| | |
|---|---|
| Polycondensate of Example 1(b) | 0.8 g |
| HCl, 0.1 N, sufficient for pH = 7 | |
| Water, sufficient amount for | 100 g |

The polycondensate, prepared according to Example 1(b), can be replaced by the same amount of any one of the polycondensates prepared according to Examples 3, 4, 7, 9 and 10.

EXAMPLE E

A hair lacquer having the following composition for dispensing with a flask pump is prepared:

| | |
|---|---|
| Polycondensate of Example 2 | 2.3 g |
| Perfume | 0.05 g |
| Ethane, sufficient amount for | 100 g |

The polycondensate, prepared according to Example 2, can be replaced by the same amount of any one of the polycondensates prepared according to Examples 4 and 5.

EXAMPLE F

A shampoo is prepared having the following composition:

| | |
|---|---|
| Polycondensate of Example 2 | 1 g |
| Surface active agent prepared according to Example 1 of French Patent 2,091,516 | 8 g |
| HCl, sufficient for pH = 6.2 | |
| Preservative, sufficient amount | |
| Water, sufficient amount for | 100 g |

EXAMPLE G

A shampoo having the following composition is prepared:

| | |
|---|---|
| Polycondensate of Example 3 | 1.5 g |
| Sodium $C_{12}$-$C_{14}$ alkyl ether sulfate oxyethylenated with 2.2 moles of ethylene oxide (25% active material) | 40 g |
| HCl, sufficient for pH = 6.4 | |
| Preservative, sufficient amount | |
| Water, sufficient amount for | 100 g |

EXAMPLE H

A shampoo having the following composition is prepared:

| | |
|---|---|
| Polycondensate of Example 4 | 0.90 g |
| Sodium hemisulfosuccinate of polyethoxylated lauryl alcohol, 40% active material, sold under the trade designation "Setacin 103 special" by Zchimmer & Schwarz | 26.30 g |
| NaOH, sufficient for pH = 6 | |
| Preservative, sufficient amount | |
| Water, sufficient amount for | 100 g |

EXAMPLE I

A shampoo having the following composition is prepared:

| | |
|---|---|
| Polycondensate of Example 5 | 3 g |
| Tridedeceth 7 carboxylic acid having the the formula $CH_3$—$(CH_2)_{11}$—$CH_2$—$(OCH_2)_6$—$OCH_2$—COOH, 90% active material, sold under the trade designation "Sandopan DTC acid" by Sandoz | 11.11 g |
| Sodium and magnesium lauryl ether sulfate, 30% active material, sold under the trade designation "Texapon ASV" by Henkel | 3 g |
| HCl, sufficient for pH = 7.5 | |
| Preservative, sufficient amount | |
| Water, sufficient amount for | 100 g |

EXAMPLE J

A shampoo having the following composition is prepared:

| | |
|---|---|
| Polycondensate of Example 5 | 2 g |
| Triethanolamine $C_{12}$-$C_{14}$ alkyl sulfate, 40% active material | 15 g |
| $C_{12}$-$C_{18}$ alcohol dimethyl carboxymethyl ammonium hydroxide, 30% active material, sold under the trade designation "Dehyton AB 30" by Henkel | 16.66 g |
| HCl, sufficient for pH = 6.5 | |
| Preservative, sufficient amount | |
| Water, sufficient amount for | 100 g |

EXAMPLE K

A shampoo having the following composition is prepared:

| | |
|---|---|
| Polyaminoamide of Example 4 | 1 g (active material) |
| Sodium $C_{12}$-$C_{14}$ alkyl ether sulfate oxyethylenated with 2.2 moles of ethylene oxide | 5 g (active material) |
| Cocamidopropylbetaine, 30% active material sold under the trade designation "TEGO-BETAIN" by Goldschmidt | 3 g (active material) |
| HCl, Sufficient for pH = 7 | |

-continued

| | |
|---|---|
| Perfume, preservative - sufficient amount | |
| Water, sufficient amount for | 100 g |

EXAMPLE L

A hair brushing lotion having the following composition is prepared:

| | |
|---|---|
| Polyaminoamide of Example 4 | 0.5 g (active material) |
| Copolymer of vinyl pyrrolidone and dimethylaminoethyl methacrylate sold under the designation "COPOLYMER 845" by GAF | 0.3 g (active material) |
| Siliconed cationic polymer, sold by Dow Corning under the designation "EMOLSION CATIONIQUE DC 929" at a concentration of 35% active material | 0.3 g (active material) |
| Lactic acid, sufficient for pH = 8.5 | |
| Ethyl alcohol, sufficient amount for | 20% volume |
| Perfume, preservative, dye - sufficient amount | |
| Water, sufficient amount for | 100 g |

Study of the Improvement of the Mechanical Resistance of Hair

Samples of bleached hair were exposed for 130 hours, to natural light. The samples were then immersed overnight in permutted water at 20° C. The load and elongation to rupture, as well as the 15% extension degree of both the exposed hair samples and control hair samples, i.e. the non-exposed samples were measured on a Lhomargy DYll traction type machine. The traction measurements were effected in water at 20° C.

These measurements registered a loss of 8% of 15% extension degree and a loss of 11% of the load at rupture for the hair samples which had been submitted to prolonged exposure to natural light, relative to the non-exposed control samples.

Bleached hair samples were then treated with a 3 weight percent aqueous solution of the polyaminoamide.

After rinsing, filtering and drying the thus treated hair samples and exposing them to natural light for 130 hours, the hair samples were immersed overnight in permutted water at 20° C. Thereafter the mechanical properties of the hair samples were measured under the same conditions described above. Only a loss of 5% of 15% extension degree relative to the non-exposed control samples was observed.

These tests evidence the protective effect against light of the polyaminoamide of the capillary fiber by measuring the reduction of the degradation of the mechanical properties of the fiber submitted to a prolonged exposure to natural light.

What is claimed is:

1. A cosmetic composition comprising in a cosmetically acceptable vehicle at least one condensate free from terminal double bonds resulting from the addition reaction between (1) a bis-acrylamide of the

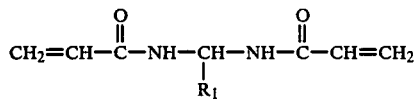
(I)

wherein $R_1$ represents hydrogen or lower alkyl having 1-4 carbon atoms, and (2) at least one sterically hindered primary diamine having the formula $$NH_2-R-NH_2 \quad (II)$$

wherein R represents a radical selected from the group consisting of

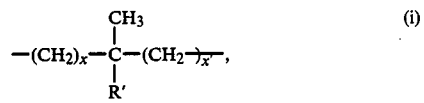
(i)

wherein x and x' are 0 or 1 and R' is hydrogen or methyl,

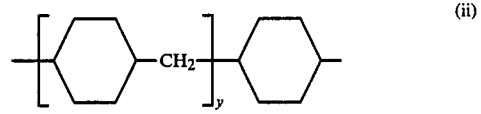
(ii)

wherein y is 0 or 1,

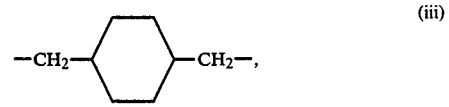
(iii)

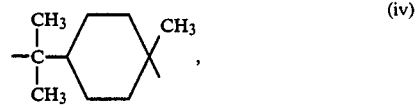
(iv)

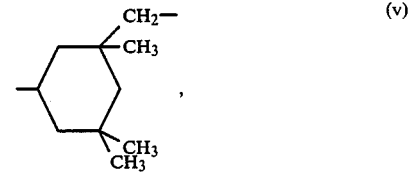
(v)

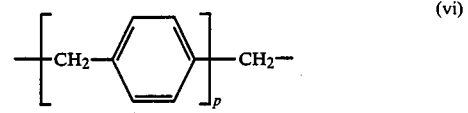
(vi)

wherein p is 1 or 2, and

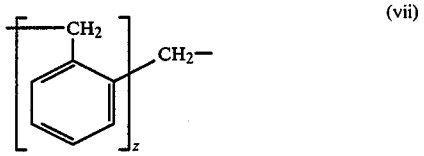
(vii)

wherein z is 1 or 2, the said condensate being saturated by hydrogenation or by addition of a thiol or an amine on the double bonds of the acrylamide residues.

2. The composition of claim 1 wherein said condensate has a molecular mass ranging from 335 to 200,000.

3. The composition of claim 1 wherein said sterically hindered diamine is selected from the group consisting of 2,2-dimethyl-1,3-diamino propane,
1,1-diamino ethane,
1,4-diamino cyclohexane,
2,2-diamino propane, 1,2-diamino-2-methyl propane,
(3-amino methyl-3,5,5-trimethyl)cyclohexylamine,
2-amino-2-(4-amino-4-methyl) cyclohexyl propane,
bis-(4-amino cyclohexyl) methane,
1,4-dimethylamino cyclohexane,
1,2-dimethylamino cyclohexane,
α,α'-diamino o-xylene,
α,α'-diamino p-xylene,
4-bis-benzylamino methane and
2-bis-benzylamino methane.

4. The composition of claim 1 wherein said bis-acrylamide is methylene bis-acrylamide, ethylidene bis-acrylamide or propylidene bis-acrylamide.

5. The composition of claim 1 wherein said condensate has the formula

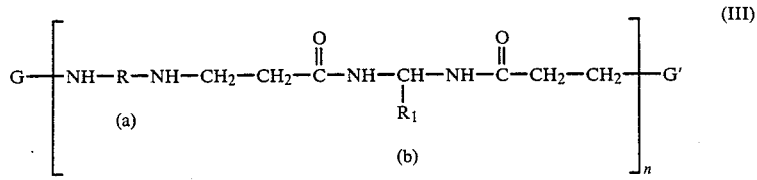

wherein
R and R₁ have the same meanings given in claim 1,
G represents hydrogen or

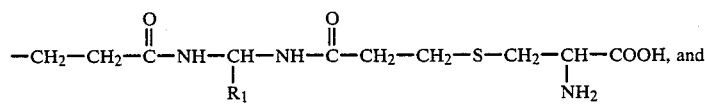

G' represents —NH—R—NH₂ wherein R has the meaning given in claim 1 or

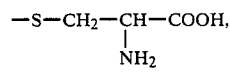

the units (a) and (b) represent 50 mole percent,
the weight percent of the functions derived from cysteine of the formula

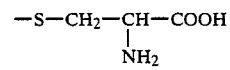

in one or both of G and G' being between about 0.15 and 30 percent, and n has an average value between 1 and 200.

6. The composition of claim 1 wherein said condensate is present in an amount ranging from 0.1 to 25 percent by weight based on the total weight of said composition.

* * * * *